United States Patent
Camisa et al.

(10) Patent No.: US 12,349,919 B2
(45) Date of Patent: Jul. 8, 2025

(54) SYSTEMS FOR ENDOSCOPIC SUBMUCOSAL DISSECTION

(71) Applicant: Covidien LP, Mansfield, MA (US)

(72) Inventors: William Camisa, Santa Clara, CA (US); Hillary K. Huszar, Redwood City, CA (US); Ellie K. Ahlquist, San Jose, CA (US); Ryan Bertwell, San Jose, CA (US); Shawn C. Daniel, Mountlake Terrace, WA (US)

(73) Assignee: Covidien LP, Mansfield, MA (US)

( * ) Notice: Subject to any disclaimer, the term of this patent is extended or adjusted under 35 U.S.C. 154(b) by 413 days.

(21) Appl. No.: 17/922,460

(22) PCT Filed: May 25, 2021

(86) PCT No.: PCT/US2021/033999
§ 371 (c)(1),
(2) Date: Oct. 31, 2022

(87) PCT Pub. No.: WO2021/242727
PCT Pub. Date: Dec. 2, 2021

(65) Prior Publication Data
US 2023/0165590 A1    Jun. 1, 2023

Related U.S. Application Data (60) Provisional application No. 63/031,620, filed on May 29, 2020.

(51) Int. Cl.
*A61B 17/128* (2006.01)
*A61B 17/122* (2006.01)
(Continued)

(52) U.S. Cl.
CPC ...... *A61B 17/1285* (2013.01); *A61B 17/1227* (2013.01); *A61B 2017/00867* (2013.01); *A61B 2017/12004* (2013.01)

(58) Field of Classification Search
CPC ............ A61B 17/1285; A61B 17/1227; A61B 17/0218; A61B 17/083;
(Continued)

(56) References Cited

U.S. PATENT DOCUMENTS

| | | |
|---|---|---|
| 2018/0279869 A1 | 10/2018 | Wales et al. |
| 2019/0099172 A1 | 4/2019 | Wales |
| 2019/0216463 A1 | 7/2019 | Dobashi et al. |

FOREIGN PATENT DOCUMENTS

| | | |
|---|---|---|
| JP | 2017176335 A | 10/2017 |
| JP | 2019154978 A | 9/2019 |

(Continued)

OTHER PUBLICATIONS

International Search Report and Written Opinion dated Sep. 23, 2021, issued in corresponding International Appln. No. PCT/US2021/033999, 15 pages.
(Continued)

*Primary Examiner* — Ryan J. Severson
(74) *Attorney, Agent, or Firm* — Carter, DeLuca & Farrell LLP (57) ABSTRACT

A surgical system for performing an endoscopic submucosal dissection includes first and second surgical clips each having first and second jaw members for grasping tissue therebetween. The first surgical clip includes a resilient member attached to one of the jaw members and configured to bow outwardly to engage tissue. The jaw members of the first surgical clip each has a pointed tip and each of the jaw members of the second surgical clip has a blunt distal tip.

13 Claims, 5 Drawing Sheets

(51) Int. Cl.
*A61B 17/00* (2006.01)
*A61B 17/12* (2006.01)

(58) Field of Classification Search
CPC ........... A61B 2017/00867; A61B 2017/12004; A61B 2017/00269; A61B 2017/034
See application file for complete search history.

(56) References Cited

FOREIGN PATENT DOCUMENTS

| | | | |
|---|---|---|---|
| JP | 2019524276 | A | 9/2019 |
| WO | 2021021987 | A1 | 2/2021 |
| WO | 2021113232 | A1 | 6/2021 |

OTHER PUBLICATIONS

European Examination Report issued in corresponding application EP 21 733 622.1 dated Sep. 24, 2024 (6 pages).
Japanese Office Action issued in corresponding application JP 2022-573234 mailed Nov. 12, 2024, together with English language translation (4 pages).

SYSTEMS FOR ENDOSCOPIC SUBMUCOSAL DISSECTION

CROSS-REFERENCE TO RELATED APPLICATIONS

This application claims the benefit of and priority to U.S. Provisional Patent Application No. 63/031,620, filed May 29, 2020, the entire contents of which is incorporated by reference herein.

FIELD

The present technology is related generally to surgical tissue clips used in endoscopic submucosal dissection.

BACKGROUND

Endoscopic removal has been accepted as a first choice of the treatment for early stage GI carcinomas because of less invasiveness and lower cost. Endoscopic submucosal dissection (ESD) allows for an en bloc removal and accurate histopathological diagnosis regardless of the size, an existence of severe fibrosis at submucosal layer, and location of a lesion. One of the benefits of ESD is lower recurrence rates compared to endoscopic mucosal resection (EMR). During some ESDs, jaw members of a hemostatic clip are engaged to tissue. After performing the removal, the jaw members are disengaged from the tissue.

SUMMARY

In one aspect, the present disclosure provides a surgical system for performing an endoscopic submucosal dissection. The surgical system includes first and second surgical clips each having first and second jaw members configured to move between an open configuration and a closed configuration to grasp tissue therebetween. The first and/or second jaw member of the first surgical clip has a pointed distal tip. The first surgical clip has a resilient member attached to one of the first or second jaw members. The resilient member is configured to transition between a stored state and a deployed state, in which the resilient member bows outwardly. Each of the first and second jaw members of the second surgical clip has a blunt distal tip.

In aspects, the distal tip of each of the first and second jaw members of the second surgical clip may have a planar distal-most edge.

In aspects, the distal tip of each of the first and second jaw members of the second surgical clip may have an arcuate distal-most edge.

In aspects, each of the first and second jaw members of the second surgical clip may include a proximal end portion, and a distal end portion having the distal tip.

In aspects, the distal tip of each of the first and second jaw members of the second surgical clip may curve inwardly toward one another.

In aspects, the proximal end portion of each of the first and second jaw members of the second surgical clip may have a chamfered proximal end.

In aspects, the second surgical clip may include a proximal body portion and the first and second jaw members of the second surgical clip may be coupled to the proximal body portion. A gap may be defined between a distal edge of the proximal body portion and the chamfered proximal end of each of the first and second jaw members of the second surgical clip.

In aspects, the first jaw member of the first surgical clip may have a proximal end portion defining a pair of holes. The resilient member may be attached to the first jaw member of the first surgical clip via the pair of holes.

In aspects, each of the pair of holes may have a greater diameter than a diameter of the resilient member.

In aspects, the resilient member may be a monolithically formed wire having first and second ends that are crimped together.

In aspects, the wire may be fabricated from a shape memory material.

In aspects, each of the first and second surgical clips may include a proximal body portion with the respective first and second jaw members movably coupled thereto.

BRIEF DESCRIPTION OF THE DRAWINGS

Objects and features of the presently disclosed surgical system will become apparent to those of ordinary skill in the art when descriptions of various embodiments thereof are read with reference to the accompanying drawings, of which.

DETAILED DESCRIPTION

The present disclosure is generally directed to a surgical system including first and second distinct surgical clips used in performing an endoscopic submucosal dissection. The first surgical clip has an elongate body, a pair of jaw members received in the elongate body and deployable therefrom, and a resilient wire coupled to one of the jaw members. The resilient wire is configured to assume a predefined, curved shape upon deployment of the first surgical clip at a surgical site. The second surgical clip differs from the first surgical clip by being devoid of the resilient wire and having blunt distal tips designed to atraumatically grasp and hold onto tissue. In some aspects, each of the first and second surgical clips may have a blunt distal tip.

During use, target tissue (e.g., a lesion) is grasped between the jaw members of the first surgical clip, and the resilient wire (in the deployed state) faces upward (e.g., away from the target tissue) at the target location. Jaw members of the second surgical clip may be used to grasp the end of the resilient wire and the second surgical clip is moved away from the first surgical clip to straighten the resilient wire. The jaw members are closed around the second targeted tissue (e.g., healthy tissue) while simultaneously grasping the resilient wire. With the resilient wire maintaining the lesion in spaced relation from the gastric wall, the lesion may be dissected. It is contemplated that the surgical system of the present disclosure may be used to treat any suitable tissue types, such as, for example, esophageal, colorectal, etc. These and other aspects of the present disclosure are described in greater detail below.

Figure 1:
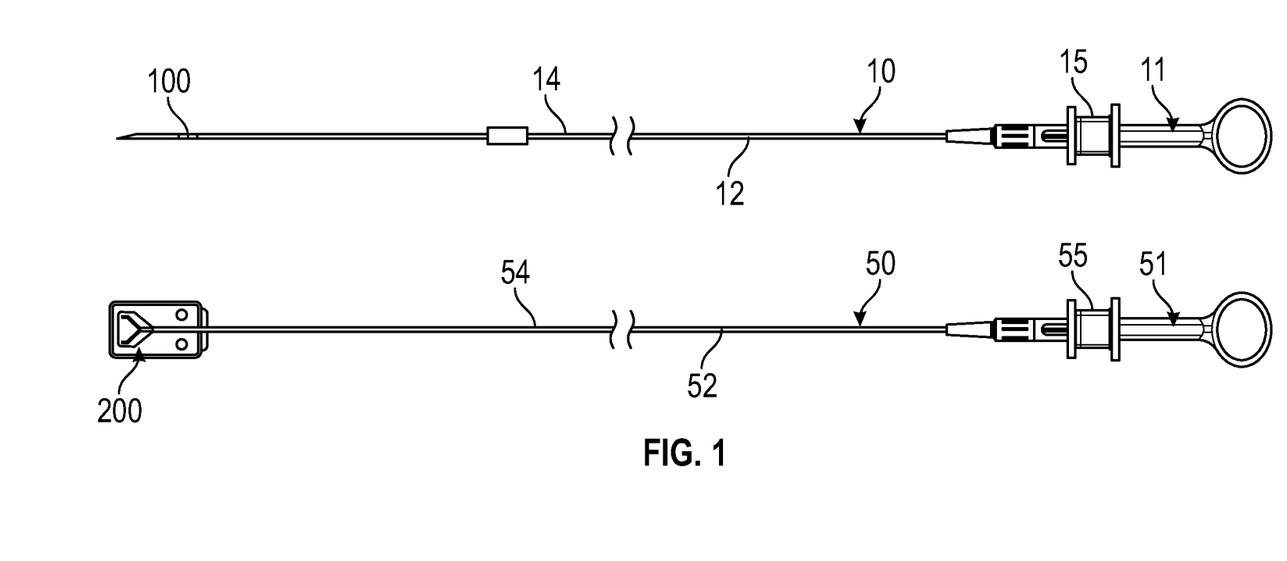
FIG. 1 is a side view illustrating a surgical system including a first hand-held surgical instrument having a first surgical clip and a second hand-held surgical instrument having a second surgical clip.

FIG. 1 illustrates a surgical system 1 including a first hand-held surgical instrument 10, such as, for example, a primary tissue grasper catheter for deploying a first surgical clip 100 (FIG. 2A), and a second hand-held surgical instrument 50, such as, for example, a secondary tissue grasper catheter for deploying a second surgical clip 200. The first surgical clip 100 is configured to grasp tissue and the second surgical clip 200 is used for simultaneously grasping tissue and a resilient member 108 of the first surgical clip 100, as will be described.

Each of the surgical instruments 10, 50 generally includes a handle assembly or actuator 11, 51 and a shaft 12, 52 extending distally from the handle assembly 11, 51. The first surgical clip 100 is detachably coupled to a distal end portion 14 of the shaft 12 of the first surgical instrument 100 and the second surgical clip 200 is detachably coupled to a distal end portion 54 of the shaft 52 of the second surgical instrument 50. In some aspects, instead of the clips 100, 200 being deployable from a hand-held instrument, the clips 100, 200 may be deployed from a surgical robotic arm.

Each of the surgical instruments 10, 50 includes an actuation mechanism, such as, for example, a puller (not shown) axially movable within the shaft 12, 52. The puller may have a proximal end operably coupled to a trigger 15, 55 of the handle assembly 11, 51 such that an actuation of the trigger 15, 55 proximally translates the puller. The puller may have a distal end detachably coupled to the surgical clip 100, 200, such that proximal translation of the puller moves the surgical clips 100, 200 from an open configuration to a closed configuration and for ultimately releasing the surgical clips 100, 200 from the remainder of the surgical instrument 10, 50. It is contemplated that the surgical instruments 10, 50 may include any suitable actuation mechanism for deploying the surgical clips 100, 200, such as a drive rod or a drive tube.

Figure 2A:
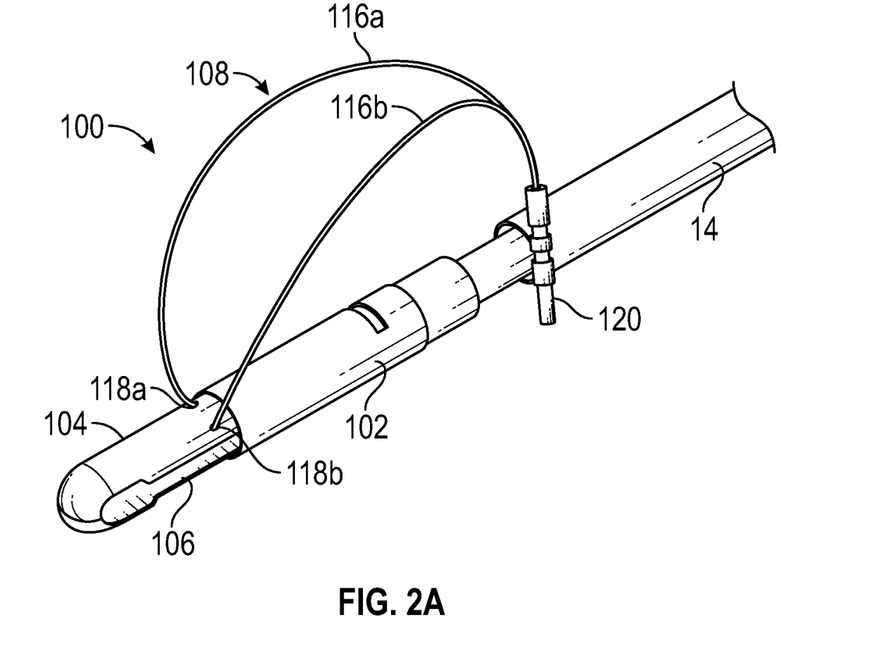
FIG. 2A is a side perspective view illustrating the first surgical clip of FIG. 1 with a resilient member thereof in a deployed state.

With reference to FIG. 2A, the first surgical clip 100 has a proximal body portion 102, such as, for example, a tubular body, first and second jaw members 104, 106 received in the proximal body portion 102, and a resilient member 108 coupled to the proximal body portion 102. The resilient member 108 of the first surgical clip 100 may be fabricated from a shape memory material, such as, for example, copper-aluminium-nickel or nickel-titanium. In some aspects, the resilient member 108 may be fabricated from any suitable material configured to maintain a predefined shape. The resilient member 108 may be fabricated from a monolithic wire of shape memory material (e.g., nickel-titanium) having first and second loose ends 116a, 116b that are passed through a pair of holes 118a, 118b in the first jaw member 104 and pulled proximally until the resilient member 108 snaps into engagement with the first jaw member 104. The holes 118a, 118b in the first jaw member 104 have a larger diameter than the diameter of the loose ends 116a, 116b to accommodate the resilient member 108 therein without altering the shape of the resilient member 108. The loose ends 116a, 116b of the resilient member 108 are crimped or otherwise joined together with a metal tube 120 and glue fillets may be added. Instead of fabricating the resilient member 108 from a folded wire, the resilient member 108 may be a thin, elongated sheet of resilient material. Other means for coupling the resilient member 108 to the jaw member 104 are also contemplated, such as, for example, adhesives, a tab, etc.

It is contemplated that the resilient member 108 has a large enough diameter (e.g., about 0.005 inches to about 0.01 inches, and in some aspects, about 0.008 inches) to provide sufficient upward lift, and a small enough diameter to not pull too hard on the muscle layer into a cutting plane. The radius of the resilient member 108 is large enough (e.g., about 7 mm) so that the user can grasp the inside of the loop of the resilient member 108 with the second surgical clip 200 to fully deploy the first surgical clip 100 and small enough to provide adequate traction. In aspects, the resilient member 108 has a large enough width (e.g., about 9 mm and about 10 mm) so that resilient member 108 lies flat on the tissue without flipping. Other constructions of the resilient member 108 are also contemplated.

Figure 2B:
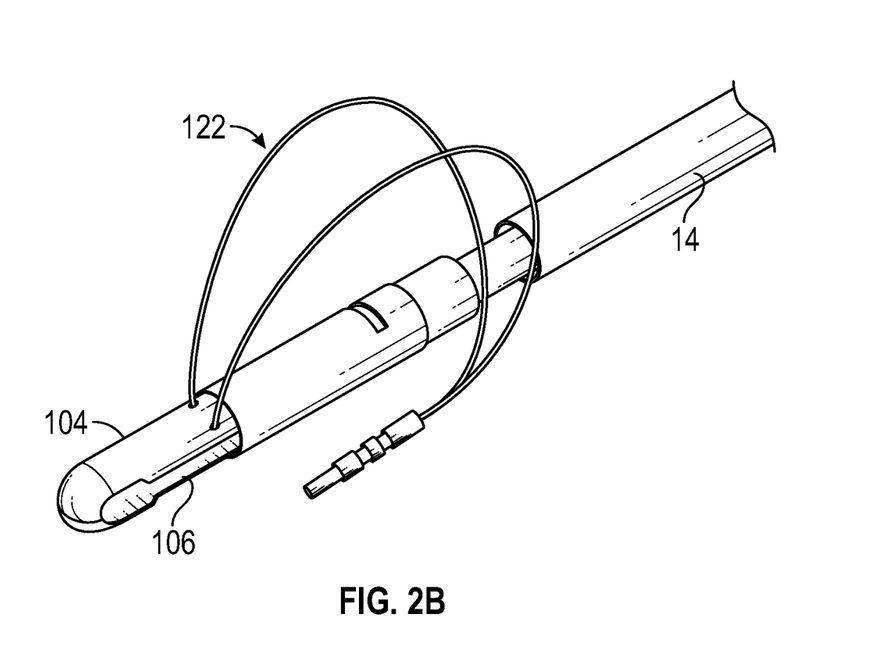
FIG. 2B is a side perspective view illustrating the first surgical clip of FIG. 1 with another type of resilient member thereof in a deployed state.

FIG. 2B illustrates another embodiment of a resilient member 122, similar to the resilient member 108 of FIG. 2A. The resilient member 122 differs from the resilient member 108 by having a greater length than the resilient member 108 (e.g., about 3.5 cm compared to about 2 cm) to be used to operate on larger lesions compared to the resilient member 108.

Figure 3A:
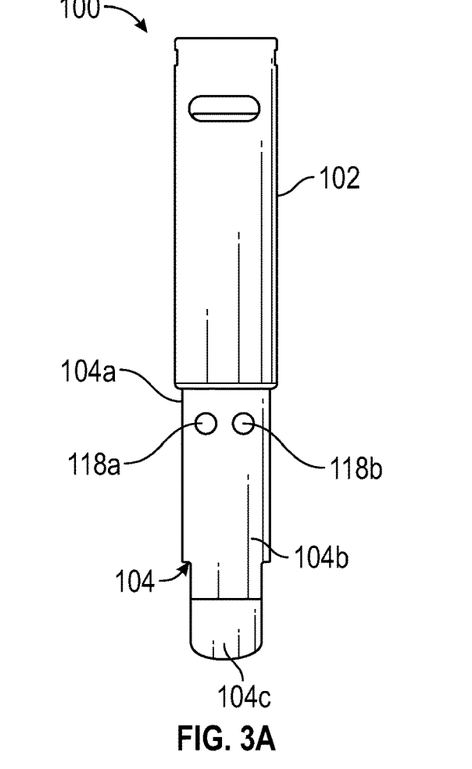
FIG. 3A is a top view of the first surgical clip of FIG. 2A shown without the resilient member.
Figure 3B:
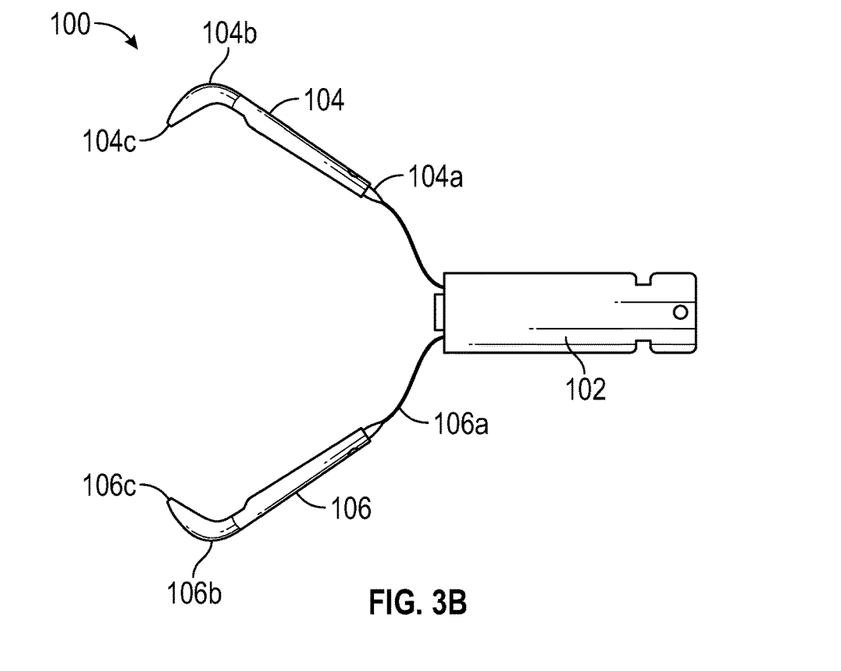
FIG. 3B is a side view of the first surgical clip of FIG. 3A illustrating the jaw members in an opened state.
Figure 3C:
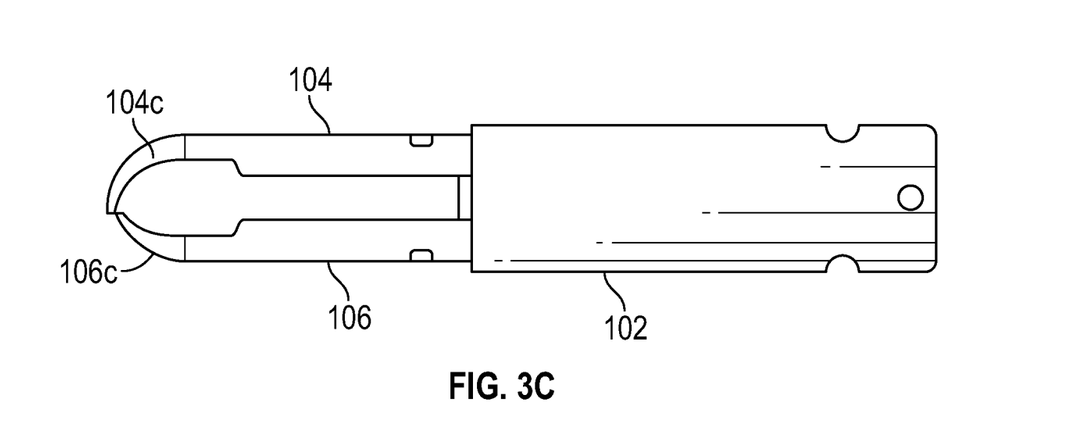
FIG. 3C is a side view of the first surgical clip of FIG. 3A illustrating the jaw members in a closed state.

With reference to FIGS. 3A-3C, the proximal body portion 102 of the first surgical clip 100 is configured to be detachably coupled to the distal end 14 (FIGS. 2A and 2B) of the shaft 12. In aspects, the shaft 12 may have a release latch (not shown) coupled to the proximal body portion 102 and an actuation mechanism (e.g., a pull rod, not shown) for actuating the release latch to deploy the first surgical clip 100 from the shaft 12.

The first and second jaw members 104, 106 are each coupled to the proximal body portion 102. Each of the first and second jaw members 104, 106 has a proximal end portion 104a, 106a slidably received in a hollow interior of the proximal body portion 102, and a distal end portion 104b, 106b disposed distally of the proximal body portion 102. The proximal end portion 104a of the first jaw member 104 defines the pair of holes 118a, 118b therethrough dimensioned for receipt of the resilient member 108.

The distal end portion 104b, 106b of each of the jaw members 104, 106 has a pointed distal tip 104c, 106c for assisting in grasping tissue between the jaw members 104, 106. The pointed distal tip 104c, 106c may be configured to penetrate tissue when the jaw members 104, 106 are in a closed state about the tissue. The jaw members 104, 106 may be resiliently biased toward an open configuration by a biasing member (not shown). Alternately, the jaw members 104, 106 may be devoid of a resilient bias. The jaw members 104, 106 are axially movable relative to the proximal body portion 102 from a proximal position, in which the distal end portion 104b, 106b of the jaw members 104, 106 are approximated toward one another, and a distal position, in which the distal end portion 104b, 106b of the jaw members 104, 106 are spaced away from one another.

Figure 4:
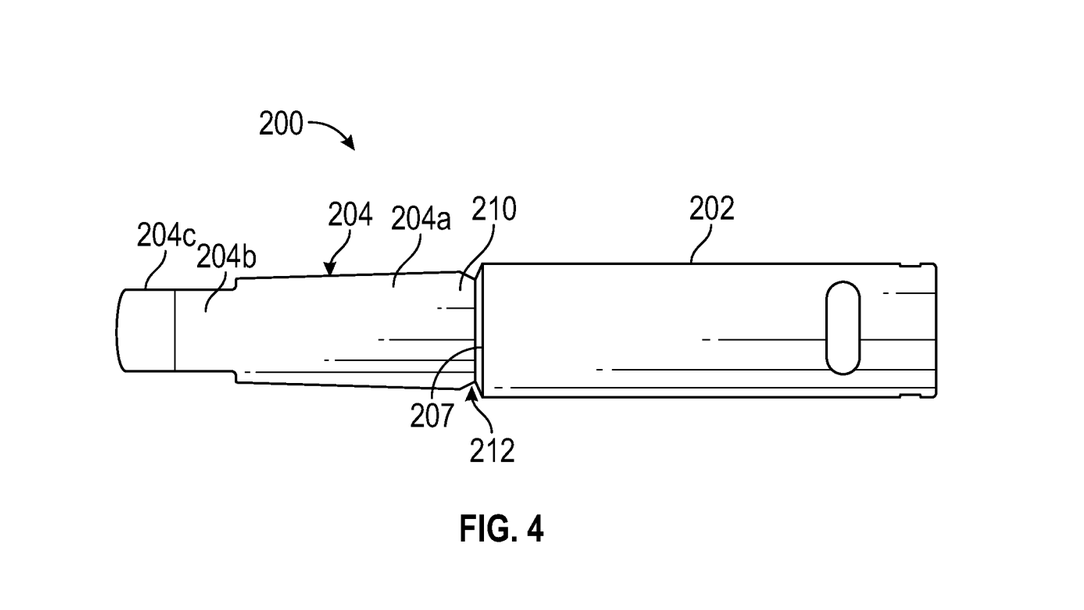
FIG. 4 is a top view of the second surgical clip of FIG. 1.
Figure 5:
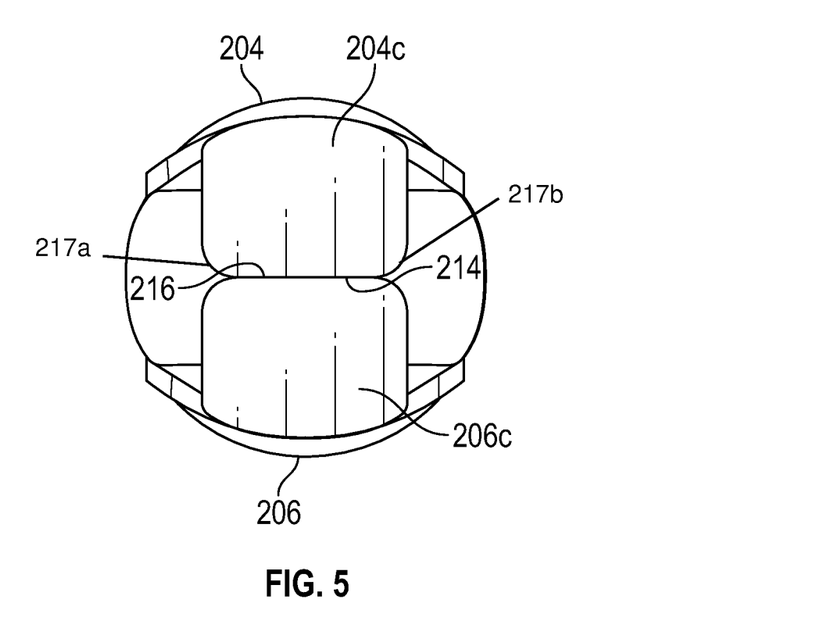
FIG. 5 is a front view illustrating a pair of jaw members of the second surgical clip of FIG. 4.

With reference to FIGS. 4 and 5, the second surgical clip 200 of the surgical system 10 includes a proximal body portion 202 detachably coupled to the flexible shaft 52 (FIG. 1) of the second surgical instrument 50 (FIG. 1) and a pair of jaw members 204, 206 coupled to the proximal body portion 202. The second surgical clip 200 differs from the first surgical clip 100 by being devoid of the resilient member 108 and being configured to atraumatically grasp tissue. Each of the first and second jaw members 204, 206 of the second surgical clip 200 may also be longer than the jaw members 104, 106 of the first surgical clip 200 and includes a proximal end portion 204a and a distal end portion 204b having a distal tip 204c, 206c. The proximal end portion 204a of each of the first and second jaw members 204, 206 of the second surgical clip 200 has a chamfered proximal end 210. A gap 212 is defined between a distal edge 207 of the proximal body portion 202 and the chamfered proximal end 210 of each of the first and second jaw members 204, 206 of the second surgical clip 200. The chamfered proximal end 210 is configured to prevent and/or resist capturing a traction wire in the gap 212 during use. In aspects, instead of being chamfered, the proximal end 210 may define a groove therein.

The distal tip 204c, 206c of each of the first and second jaw members 204, 206 of the second surgical clip 200 curves inwardly toward one another. The distal tip 204c, 206c of each of the first and second jaw members 204, 206 of the second surgical clip 200 has a planar distal-most edge 214, 216 disposed between curved lateral ends 217a, 217b. The lateral ends 217a, 217b have a relatively large radius (e.g., from about 0.05 mm to about 0.4 mm), thereby exhibiting a generally flat curvature. The curved lateral ends 217a, 217b may be formed by stamping or a secondary processor such as deburring or polishing. The distal-most edges 214, 216 are configured to prevent penetrating or otherwise damaging tissue when tissue is grasped between the distal tips 204c, 206c. It is contemplated that the clamping force between the distal tips 204c, 206c does not exceed about 1.9 lbs at a gap between distal tips 204c, 206c of about 1 mm.

Unexpectedly, it was found that by making the distal-most edge 214, 216 of the distal tips 204c, 206c blunt (e.g., flat and/or curved and devoid of any sharp points or abrupt projections that may damage tissue), the jaw members 204, 206 remained capable of effectively grasping tissue therebetween with the added benefit of not causing any damage to the healthy tissue being grasped. Prior hemostatic clips have pointed or sharp tips that either penetrate or otherwise damage tissue. Typical hemostatic clips are not removed post-procedure. Rather, they are left behind on tissue.

Figure 6:
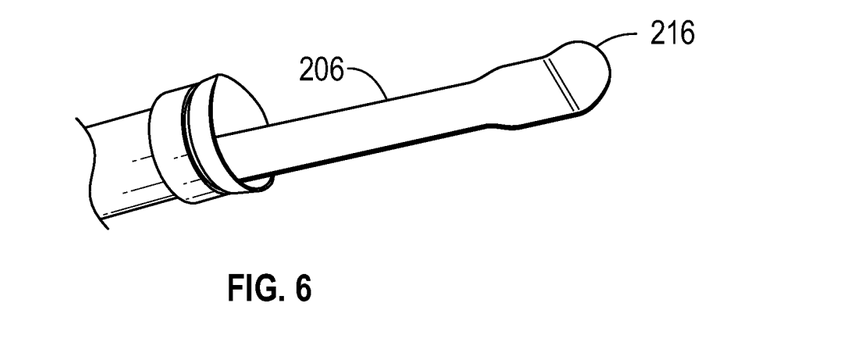
FIG. 6 is a top, perspective view illustrating another embodiment of a jaw member of the second surgical clip.

In some aspects, as shown in FIG. 6, the distal-most edge 214, 216 of the distal tips 204c, 206c may be arcuate rather than flat and/or have a continuous curvature therealong. For example, the entire length of the distal tips 204c, 206c may be curved and have a radius between about half of the width of the distal tip 204c to about 0.05 mm.

In use, the first surgical instrument 10, with the first surgical clip 100 attached thereto, is inserted into and passed through a working channel of an endoscope (not explicitly shown). In some aspects, the first surgical clip 100 may be received in an introducer, which is passed through the working channel of the endoscope. After passing through the endoscope, the first surgical clip 100 is directed to a targeted gastrointestinal tissue by manipulation of the endoscope and first surgical instrument 10.

With the first surgical clip 100 coupled to the shaft 12 and the jaw members 104, 106 in the open configuration, the first surgical clip 100 is positioned adjacent tissue (e.g., a lesion). The tissue is positioned between the jaw members 104, 106, whereupon the puller of the surgical instrument 10 retracts the jaw members 104, 106 proximally through the proximal body portion 102. An inner wall of the proximal body portion 102 acts on the jaw members 104, 106 to move the jaw members 104, 106 toward the closed configuration about the tissue. With the tissue grasped between the jaw members 104, 106, the puller is further retracted to detach the puller from the jaw members 104, 106, thereby releasing the proximal body portion 102 of the first surgical clip 100 from the shaft 12 and leaving the first surgical clip 100 at the surgical site. Other mechanisms for releasing the first surgical clip 100 from the shaft 12 are also contemplated.

Upon releasing the first surgical clip 100 from the shaft 12, the resilient member 108 of the first surgical clip 100 is allowed to transition from a stored state, in which the resilient member 108 is constrained within the shaft 12, to a deployed state. In the stored state, the resilient member 108 assumes a generally linear shape, and in the deployed state, the resilient member 108 moves toward its predefined, arcuate shape, in which the resilient member 108 bows outwardly from the proximal body portion 102.

The second surgical instrument 50, with the second surgical clip 200 attached thereto, may be introduced into the endoscope and advanced through the working channel until a distal end of the second surgical clip 200 is visualized. The first and second jaw members 204, 206 of the second surgical clip 200 are opened. The second surgical instrument 50 or endoscope are then manipulated to grab the resilient member 108 of the first surgical clip 100 with the jaw members 204, 206 of the second surgical clip 200. While holding the resilient member 108 of the first surgical clip 100 between the jaw members 204, 206 of the second surgical clip 200, the second surgical instrument 50 is moved away from the first surgical clip 200 until the resilient member 108 is flattened out (e.g., transitioned to the stored state) and pressed against the tissue. By flattening out the resilient member 108, the outward bias of the resilient member 108 lifts the first surgical clip 100 attached to the lesion to separate the lesion from the tissue wall. The separation of the lesion from the tissue wall helps during excising of the lesion. The jaw members 204, 206 of the second surgical clip 200 are closed around a second targeted tissue (e.g., healthy tissue), whereby the second surgical clip 200 simultaneously grasps the healthy tissue and the resilient member 108 of the first surgical clip 100. When proper positioning is confirmed, the second surgical clip 200 is detached from the rest of the second surgical instrument 50.

Upon completion of use of the system 1, the second surgical clip 200 may be separated from the tissue by pulling the second surgical clip 200 with forceps or other available endoscopic tools. Since the distal tip 204c, 206c of the jaw members 204, 206 of the second surgical clip 200 are blunt, pulling of the second surgical clip 200 does not tear or otherwise damage the tissue. After separation of the second surgical clip 200 from the tissue, the second surgical clip 200, the first surgical clip 100, and the excised tissue will be attached together and are removed from the patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:

1. A surgical system for performing an endoscopic submucosal dissection, comprising:
    a first surgical clip including:
        first and second jaw members configured to move between an open configuration and a closed configuration to grasp tissue therebetween; and
        a resilient member attached to one of the first or second jaw members and configured to transition between a stored state and a deployed state, in which the resilient member bows outwardly; and a second surgical clip including first and second jaw members configured to move between an open configuration and a closed configuration to grasp tissue therebetween, wherein each of the first and second jaw members of the second surgical clip has a blunt distal tip.

2. The surgical system according to claim 1, wherein the distal tip of each of the first and second jaw members of the second surgical clip has a planar distal-most edge.

3. The surgical system according to claim 1, wherein the distal tip of each of the first and second jaw members of the second surgical clip has an arcuate distal-most edge.

4. The surgical system according to claim 1, wherein each of the first and second jaw members of the second surgical clip includes:

a proximal end portion; and
a distal end portion having the distal tip.

5. The surgical system according to claim 4, wherein the distal tip of each of the first and second jaw members of the second surgical clip curves inwardly toward one another.

6. The surgical system according to claim 4, wherein the proximal end portion of each of the first and second jaw members of the second surgical clip has a chamfered proximal end.

7. The surgical system according to claim 6, wherein the second surgical clip includes a proximal body portion, the first and second jaw members of the second surgical clip being coupled to the proximal body portion, a gap being defined between a distal edge of the proximal body portion and the chamfered proximal end of each of the first and second jaw members of the second surgical clip.

8. The surgical system according to claim 1, wherein the first jaw member of the first surgical clip has a proximal end portion defining a pair of holes, the resilient member being attached to the first jaw member of the first surgical clip via the pair of holes.

9. The surgical system according to claim 8, wherein each of the pair of holes has a greater diameter than a diameter of the resilient member.

10. The surgical system according to claim 8, wherein the resilient member is a monolithically formed wire having first and second ends that are crimped together.

11. The surgical system according to claim 10, wherein the wire is fabricated from a shape memory material.

12. The surgical system according to claim 1, wherein the first surgical clip includes a proximal body portion, the first and second jaw members of the first surgical clip movably coupled to the proximal body portion, the second surgical clip including a proximal body portion, the first and second jaw members of the second surgical clip being movably coupled to the proximal body portion of the second surgical clip.

13. The surgical system according to claim 1, wherein at least one of the first or second jaw members of the first surgical clip has a pointed distal tip.

* * * * *